United States Patent [19]

Székely et al.

[11] Patent Number: 5,273,953
[45] Date of Patent: Dec. 28, 1993

[54] PESTICIDAL COMPOSITIONS COMPRISING ETHOXYLATED CITRIC OR TARTARIC ACID DERIVATIVES AS STABILIZING SURFACTANTS

[75] Inventors: István Székely, Dunakeszi; Lajos Nagy, Szentendre; Péter Bohus, Budapest; András Szego, Budapest; Lászlo Pap, Budapest; Tamásné Mármarosi, Biatorbágy, all of Hungary

[73] Assignee: Chinoin Gyogyszer es Vegyeszeti Termekek Gyara Rt., Budapest, Hungary

[21] Appl. No.: 663,911

[22] PCT Filed: May 7, 1990

[86] PCT No.: PCT/HU90/00032

§ 371 Date: Mar. 7, 1991

§ 102(e) Date: Mar. 7, 1991

[87] PCT Pub. No.: WO90/13222

PCT Pub. Date: Nov. 15, 1990

[30] Foreign Application Priority Data

May 8, 1989 [HU] Hungary ............... 2193/89

[51] Int. Cl.$^5$ ............................. A01N 25/22
[52] U.S. Cl. ................... 504/116; 424/405; 514/521; 514/531
[58] Field of Search ............. 514/521, 531; 560/200; 562/584; 71/DIG. 1; 504/116; 424/405

[56] References Cited

U.S. PATENT DOCUMENTS

| | | |
|---|---|---|
| 3,898,075 | 8/1975 | Freund et al. ........... 71/DIG. 1 |
| 4,048,065 | 9/1977 | Suen et al. ................... 210/58 |
| 4,668,507 | 5/1987 | Tomkins et al. ............ 424/45 |
| 4,673,509 | 6/1987 | Davis et al. ............... 210/699 |
| 5,043,163 | 8/1991 | Pap et al. .................. 424/405 |
| 5,082,591 | 1/1992 | Marchetto et al. ..... 71/DIG. 1 |

FOREIGN PATENT DOCUMENTS 209910 1/1987 European Pat. Off.
57-130903 8/1982 Japan.

OTHER PUBLICATIONS

Spencer, E. Y. *Guide to Chemicals Used in Crop Protection* Research Branch, Agriculture Canada, 1981, p. 152.

Primary Examiner—Richard L. Raymond
Assistant Examiner—S. Mark Clardy
Attorney, Agent, or Firm—Herbert Dubno; Jonathan Myers

[57] ABSTRACT

The invention relates to a plant protecting or veterinary or additive composition, containing beside the active ingredient and other usually applied auxiliaries, such as solid and liquid carrier(s), surface active agent(s) and further additive(s), one or more surface active agent(s) of the general formulae (I)

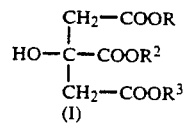

or (II),

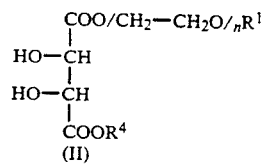

or a mixture thereof, wherein R, R$^2$, R$^3$ and R$^4$ are independently from each other hydrogen atom, an organic or inorganic cation or a group of the general formula —(CH$_2$—CH$_2$—O)$_n$R$^1$, wherein
R$^1$ is a C$_{10-20}$ alkyl group and
n is an integer from 4 to 20, with the provisio that from among the substituents R, R$^2$ and R$^3$ at least one is a group of the general formula (CH$_2$—CH$_2$O)$_n$R$^1$.

7 Claims, No Drawings

PESTICIDAL COMPOSITIONS COMPRISING ETHOXYLATED CITRIC OR TARTARIC ACID DERIVATIVES AS STABILIZING SURFACTANTS

The invention relates to plant protecting preparations, veterinary preparations and additive preparations admixable with plant protecting and veterinary preparations containing as surface active agents compounds of the formulae (I)

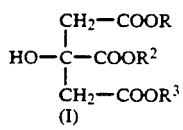

and (II),

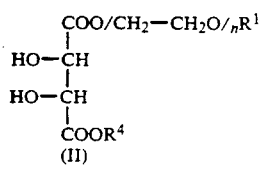

The invention also relates to the preparation of such composition. The meaning of the substituents in the formulae (I) and (II) are as follows:

R, $R^2$, $R^3$ and $R^4$ are independently hydrogen an organic or inorganic cation, or a group of the formula $-(CH_2CH_2-O)_nR^1$, wherein n is an integer from 4 to 20, and $R^1$ is a $C_{10-20}$ alkyl group.

The inorganic cation is advantageously a sodium potassium, calcium or magnesium cation. The organic cation is advantageously a cation deriving from an amine, such as triethanolamine or diethanolamine.

The surface active agents of the formulae (I) and (II) used in the preparations according to the invention and their use in cosmetic and detergent therapeutical preparations is disclosed in the published Hungarian Patent specification T/40994.

The compounds of the formulae (I) and (II) can be prepared by ethoxylating a fatty alcohol corresponding to $R^1$ (mean ethyleneoxide number is n), whereafter it is condensed with citric or tartaric acid and finally a salt is formed as required with an alkaline component supplying the suitable cation (published Hungarian Patent Specification T/40994).

We have found that the surface active agents of the formulae (I) and (II) can be advantageously used in plant protecting and veterinary preparations, respectively.

According to the invention from the surface active agents of the formulae (I) and (II) also additive preparations without any active ingredient can be prepared, which can be admixed at the time of application with the plant protecting or veterinary preparation to be applied.

The surface active agents of the formulae (I) and (II) exert in the preparations according to the invention the following positive effects:

they slow down the chemical decomposition of the active ingredient, and thus exert a stabilizing effect;
they influence the formation of the adsorptive layer (build up; structure modification);
they optimize the reological properties of the preparations, and increase the stability of the dispersion;
in some cases they give rise to a liquid crystalline structure, advantageous from the view-point of the dispersion of active ingredient and stability of the preparation;
they exert a wetting, solubilizing, penetration increasing effect;
they modify the transport character (diffusion, etc.), thereby making them suitable for the penetration of capsules;
they increase the chemical and physical compatibility of the active ingredients, etc.; and
from toxicological point of view they are very favourable, they have no poisonous effect and, biologically they are totally decomposable (a biodegradation of 100%).

The preparations according to the invention contain the surface active agents of the formulae (I) and (II) in the following amounts:

| | |
|---|---|
| plant protecting preparations | 0.1–10 mass % |
| veterinary preparations | 0.1–10 mass % |
| additive preparations | 0.1–50 mass % |

The plant protecting preparations according to the invention may contain as active ingredient some fungicidal, herbicidal, insecticidal, nematocidal, acaricidal or plant growth regulating agents, such as:

Maneb: [manganese-ethylene-bis(dithiocarbamate)-polymer]

Zineb: [zinc-ethylene-bis(dithiocarbamate)-polymer]

Manozeb: [complex of manganese-ethylene-bis(dithiocarbamate-polymer formed with zinc salt]

Metiram: zinc-polyethylene-thiuram-disulfide complex

Propineb: [zinc-propylene-bis(dithiocarbamate)-polymer]

Kaptan: [1,2,3,6-tetrahydro-N-(trichloromethyl-thio)phthalimide]

Procimidon: [N-(3,5-dichlorophenyl)-1,2-dimethyl-cyclo-propane-1,2-dicarboximide]

Kaptafol: N-(1,1,2,2-tetrachloro-ethylthio)-tetrahydrophthalimide

Folpet: N-(trichloro-methyl-thio)-phthalimide

Anilazin: [2,4-dichloro-6-(2-chloroaniline)-1,3,5-triazine]

Flutriafol: (RS)-2,4'-difluoro-α-(1H-1,2,4-triazole-1-ylmethyl)-benzhydryl-alcohol Diklofluanid: N,N-dimethyl-N'-phenyl-N'-(fluoro-dichloro-methyl-thio)-sulphamide Triforin: N,N'-bis-(1-formamido-2,2,2-trichloro-ethyl)-piperazine Vinklozolin: 3-(3,5-dichloro-phenyl)-5-methyl-vinyl-1,3-oxazolidine-2,4-dione Dodin: dodecyl-guanidine-acetate Pirazofos: 2-(0,0-diethyl-thiophosphoryl)-5-methyl-6-carbethoxy-pyrazolo-(1,5-a)-pyrimidine Bupirimat: 2-ethyl-amino-6-methyl-5-n-butyl-4-yldimethyl-sulfamate Fenarimol: α-(2-chloro-phenyl)-α-(4'-chloro-phenyl)-5''-pyrimidyl-methanol Benomyl: 1-butyl-carbamoyl-benzimidazole-2-methylcarbamate Fuberidazol: 2-(2-furyl)-benzimidazole Thiabendazol: 4-(4-thiazolyl)-1H-benzimidazole Propiconazol: 1-[2-(2,4-dichlorophenyl)-4-propyl-1,3-dioxolane-2-yl-methyl]-1H-1,2,4-triazole Triadimephon: 1-(4-chloro-phenoxy)-1-(1H-1,2,4-triazole-1-yl)-3,3-dimethyl-2-butanone Triadimenol: 1-(4-chloro-phenoxy)-1-(1H-1,2,4-triazole-1-yl)-3,3-dimethyl-2-butanol Bitartanol: β-(1,1'-biphenyl-4-yl-oxy)-β-(1,1-dimethyl-ethyl)-1H-triazole-1-ethanol Dichlorobutrazol: 1-(2,4-dichloro-phenyl)-4,4-dimethyl-2-(1,2,4-triazole-1-yl)-pentane-3-ol Thiophanate-methyl: 1,2-bis-(3-methoxy-carbonyl-thioureido)-benzene Tridemorph: 4-tridecyl-2,6-dimethyl-morpholine Carbendazim: 2-(methoxy-carbonyl-amino)-benzimidazole Phenpropiomorph: 4-(3-[4-(1,1-dimethyl-ethyl)-phenyl]-2-methyl)-propyl-2,6-cis-dimethylmorpholine Metalaxyl: D,L-N-(2,6-dimethyl-phenyl)-N-(2'-methoxyacetyl)-alanine-methyl-ester Prochlorase: N-propyl-N-[2-(2,4,6-trichloro-phenoxy)-ethyl]-imidazole-1-carboxamide Permethrin: (±)-cis,transz-3-3(2,2-dichloro-vinyl)-2,2-dimethyl-cyclopropanic acid-3-phenoxy-benzyl-ester Cypermethrin: 2,2-dimethyl-3-(2,2-dichloro-vinyl)-cyclopropane carboxylic acid-(α-cyano-3-phenoxybenzyl)-ester Deltamethrin: (1R, 3R)-3-(2,2-dibromo-vinyl)-2,2-dimethyl-cyclopropane carboxylic acid-(S)-α-cyano-m-phenoxy-benzyl-ester Bifenthrin: (2-methyl)-1,1'-biphenyl(-3-il)methyl-3-(2-chloro-3,3,3-trifluoro-1-propenyl)-2,2-dimethyl-cyclopropane-carboxylate Fempropathrin: α-cyano-3-phenoxybenzyl-2,2,3,3-tetramethyl-cyclopropane-carboxylate Malathion: 0,0-dimethyl-S-(1,2-dicarbethoxy-ethyl)-dithiophosphate Chlorphenvinphos: 0,0-diethyl-1-(2,4-dichloro-phenyl)-2-chloro-vinyl-phosphate Chlorpiriphos: 0,0-diethyl-0-(3,5,6-trichloro-2-pyridyl)-thiophosphate Dichlorphos: 0,0-dimethyl-2,2-dichloro-vinyl-phosphate Dimetoate: 0,0-dimethyl-S-(N-methyl-carbamoyl-methyl)-dithiophosphate Phenitrotion: 0,0-dimethyl-0-(3-methyl-4-nitro-phenyl)-thiophosphate Aldicarb: 2-methyl-2-methylthio-propionaldehyde-0-methyl-carbamoyl-oxume Carbaryl: N-methyl-1-naphthyl-carbamate Diazinon: 0,0-diethyl-0-(2-isopropyl-4-methyl-pyrimidinyl)-thiophosphate Bensultap: S,S'-[2-(dimethyl-amino)-trimethylene]bis-(benzene-thiosulphonate)

Endosulphane: 1,4,5,6,7,7-hexachloro-bicyclo-(1,1,2)-5-heptane-2,3-bis-(oxymethylene)-sulphite Phenvalerate: α-cyano-m-phenoxy-benzyl-α-isopropyl-p-chloro-phenyl-acetate Metidation: 0,0-dimethyl-S-(2-methoxy-1,3,4-thiadiazole-5-(4H)-onyl)-(4)-methyl)-dithiophosphate Metomyl: S-methyl-N-(methyl-carbamoyl-oxy)-thioacetimidate Mevinphos: 0,0-dimethyl-0-(1-methyl-2-carbomethoxy)-vinyl-phosphate Trichlorphon: 0,0-dimethyl-1-hydroxy-2,2,2-trichloro-ethyl-phosphonate Terbuphos: 0,0-diethyl-S-tert-butyl-thiomethyl)-phosphordithioate Quinalphos: 0,0-diethyl-0-[quinoxalinyl(2)-]thionphosphate Pyrimiphos-methyl: 0,0-dimethyl-0-(2-diethyl-amino-4-methyl-pyrimidine-6-yl)-thiophosphate Phosalon: 3-0,0-diethyl-dithiophosphoryl-methyl-6-chloro-benzoxazolone Chinmix: 1RcisS+1ScisR and 1RtransS+1StransR enantiomer pairs of (RS)-α-cyano-3-phenoxybenzyl(1RS)-cis-trans-3-(2,2-dichlorovinyl)-2,2-dimethyl-cyclopropane-carboxylate Transmethrin: 1RtransS and 1StransR enantiomer pairs of (RS)-α-cyano-3-phenoxybenzyl (1RS)cis-trans-3-(2,2-dichlorovinyl)-2,2-dimethyl-cyclopropane-carboxylate.

The plant protecting preparations according to the invention can be formulated in the following forms: emulsion forming preparation (EC): wettable powders (WP); dispersible granulate (WG); suspension concentrate (SC) ULV preparation; concentrated aqueous solution (SL); microemulsion (EW); capsule-suspension (CS).

The veterinary preparations according to the invention can be formulated advantageously in the following forms: injection solutions, solutions suitable for oral dosage, concentrate-preparations, emulsions, suspensions, powders, granulates, pilules, tablets, boles, aerosols, pour-on and spot-on preparations.

The additive preparations according to the invention can be formulated advantageously in the following forms: aqueous solutions (SL), anhydrous concentrates (mixture with other surface active agents and/or with components of other function, e.g. with a diluting component, a solvent, a filling agent.)

In the course of the preparation of compositions according to the invention technologies generally used for the preparation of said formulations can be applied. The preparations according to the invention are containing or can contain beside the surface active agents of the formulae (I) and (II) other generally used additives, such as solid or liquid carriers, surface active agents and other additives.

The surface active agents of the formulae (I) and (II) may be—depending on the meaning of substituents R, $R^2$ and $R^3$—of anionic or nonionic type. The surface active agents of the formula (I) are of anionic type, in which one or two of the substituents R, $R^2$ and $R^3$ are a hydrogen atom, or they represent an organic or inorganic cation. Those compounds of the formula (II) are of the anionic type, in which $R^4$ represents a hydrogen atom or an organic or inorganic cation.

The solubility of the surface active agents of the formulae (I) and (II) depends on the quality of the cations taking part in the salt formation.

In the course of the preparation of compositions according to the invention the compounds of the formulae (I) and/or (II) can be applied without dilution or diluted, in the last case in the form of aqueous solutions.

In an aqueous medium it is possible even in a relatively low concentration to form solutions of a mean viscosity. One of the advantages of the new tensides is that their solutions are barely foaming.

In the case using the compounds of the formulae (I) and (II) in an aqeuous medium, it is preferable to adjust the pH between 5 and 7, but a more acidic medium (pH 2-5) is also suitable.

(Naturally the pH must be chosen in a way, that it must be tolerable to the active ingredient, too.)

The compounds of the formulae (I) and (II) have very different properties depending on the meaning of R, $R^1$, $R^2$, $R^3$ and n, so they can be applied widely.

In Table I the properties of two types, which are excellently soluble in water are summarized:

TABLE I

|  | disodium-monolaureate-7-citrate | sodium dilaureate-7-citrate |
|---|---|---|
| Cation | Na | Na |
| EO | 7 | 7 + 7 |
| type of ester | mono | di |
| solvent | water | water |
| dry substance 50° C., 16$^h$) | 25 ± 1 | 25 ± 1 |
| water % | 75 ± 1 | 75 ± 1 |
| viscosity 20° C. mP | about 30 | about 700 |
| pH (1% of active ingredient in water) | 6.5 ± 0.3 | 6.5 ± 0.3 |
| surface tension at 20° C. (dyn/cm) | | |
| 0.25 g/l active ingredient | 33.2 | 31.5 |
| 1.0 g/l active ingredient | 32.3 | 31.0 |

In Table II some compounds of the formulae (I) and (II) are described suitable for application in the preparations according to the invention.

TABLE II

| Component (code) | Ester M = mono D = di T = tri | Type acid = 8 salt | R$_1$ alkyl | n | Starting acid | Surface active agent quantity mass % | Solvent, carrier quantity mass % |
|---|---|---|---|---|---|---|---|
| A | M | H | lauryl C$_{12}$ | 7 | citric acid | 100 | — |
| B | M | Na | lauryl C$_{12}$ | 8 | citric acid | 25 | water |
| C | M | Na | lauryl C$_{12}$ | 20 | citric acid | 100 | — |
| D | M | TEA | lauryl C$_{12}$ | 10 | citric acid | 100 | — |
| E | M | TEA | lauryl C$_{12}$ | 4 | citric acid | 60 | Vessalon |
| F | D | H | C$_{16}$ | 7 + 7 | citric acid | 100 | — |
| G | D | TEA | C$_{14}$ | 4 + 4 | citric acid | 100 | — |
| H | D | TEA | C$_{18}$ | 6 + 6 | citric acid | 80 | xylene |
| I | D | Ca | C$_{12}$ | 7 + 7 | citric acid | 70 | butyl diglycol |
| J | T | — | C$_{12}$ | 6 + 6 + 6 | citric acid | 100 | — |
| K | M | H | C$_{12}$ | 6 | tartaric acid | 100 | — |
| M | D | — | C$_{12}$ | 5 + 5 | tartaric acid | 100 | — |
| N | D | — | C$_{10}$ | 8 + 8 | tartaric acid | 100 | — |
| P | D | — | C$_{12}$ | 7 + 7 | tartaric acid | 70 | xylene |
| R | M | Na | C$_{12}$ | 6 | citric acid | 80 | DMA |
| O | M | Na | C$_{12}$ | 6 | tartaric acid | 25 | water |
| S | D | Na | C$_{12}$ | 6 + 6 | citric acid | 25 | water |
| T | D | Na | C$_{12}$ | 6 + 6 | citric acid | 100 | — |
| X | M | K | C$_{12}$ | 9 + 9 | tartaric acid | 40 | water |
| Y | T | — | C$_{12}$ | 4 + 4 + 4 | citric acid | 50 | Vessalon |
| Z | M | Ca | C$_{12}$ | 7 | citric acid | 100 | — |
| V | D | TEA | C$_{12}$ | 5 + 5 | citric acid | 100 | — |
| W | D | MEA | C$_{12}$ | 5 + 5 | citric acid | 50 | water |

The surface activity of compounds of the formulae (I) and (II) is excellent, that is they decrease suitably the water/air interfacial tension even in a low concentration.

This is illustrated in Table III.

TABLE III

| | Surface tension dyn/cm | |
|---|---|---|
| | 0.25 g/l | 1 g/l |
| Compound of the formula (I) code | | |
| S | 1.5 | 31.0 |
| B | 33.2 | 32.3 |
| O | 34.0 | 33.6 |

TABLE III-continued

| | Surface tension dyn/cm | |
|---|---|---|
| | 0.25 g/l | 1 g/l |
| Sodium-dodecyl-benzene-sulphonate | 41.2 | 34.2 |
| Sodium-lauryl-ether-sulphate (EO:2) | 35.0 | 31.8 |

The preparations according to the invention are illustrated by the following examples, without any limitation as to the scope of invention.

1. Emulsion forming agents (In the following preparations the components according to the invention (A, F, K) increase the chemical stability of the active ingredients.)

| a.) Dichlorvos (96%) | 20.85 mass % |
|---|---|
| Component A | 2 mass % |
| Emulson AG/CAL | 3 mass % |
| Emulson AG/EL | 4 mass % |
| Xylene | ad 100 mass % | where Emulson AG/CAL = calcium-dodecyl-benzene-sulphonate (a 60% active ingredient solution).

| b.) Cypermethrin (90%) | 11.1 mass % |
|---|---|
| Component F | 1.5 mass % |
| Emulson AG/CAL | 2.5 mass % |
| Emulson AG/COH | 2.5 mass % |
| Solvesso 150 | ad 100 mass % | where Emulsion AG/COH = ethoxylated EO:25 hydrogenated (saturated) castor oil derivative.
Solvesso 150 = aromatic solvent.

| c.) Phenmedipham (97%) | 16.1 mass % |
|---|---|
| Component K | 2.0 mass % |
| Emulsogen AG/CAL | 5.0 mass % |
| Emulson AG/2B | 4.0 mass % |
| Emulson AG/7B | 9.0 mass % |
| Isophoron | ad 100 mass % | where
Emulson AG/2B = ethoxylated nonylphenol, EO:2
Emulson AG/98 = ethoxylated nonylphenol, EO:9

2. Emulsion forming agents (EC)

(In the following preparations the components according to the invention (G, Z, H, J, P, M) possess emulsifying activity.)

| a.) Metolachcor (96%) | 75 mass % | 75 mass % |
|---|---|---|
| Component G | 6 mass % | 3 mass % |
| Emulson AG/CAL | — | 2 mass % |
| Emulson AG/PE | 4 mass % | — |
| Emulson AG/EL | — | 5 mass % |
| Xylene | ad 100 mass % | ad 100 mass % | where Emulson AG/PE = an EO + PrO condensate

| b.) Cypermethrin (90%) | 11. mass % | 20.8 mass % |
|---|---|---|
| Component Z | 5 mass % | 5 mass % |
| Emulson AG/CAL | 1 mass % | 2.5 mass % |
| Emulson AG/EL | 2 mass % | 2.5 mass % |
| Solvesso 150 | — | ad 100 mass % |
| Xylene | ad 100 mass % | — |
| Cyclohexanone | — | 10 mass % |

| c.) Quinalphos (in 50% xylene) | 50 mass % | 50 mass % |
|---|---|---|
| Component H | 6 mass % | 4 mass % |
| Component J | 2 mass % | 2 mass % |
| Component P | 2 mass % | — |
| Component M | — | 4 mass % |
| Xylene | ad 100 mass % | ad 100 mass % |

3. Aqueous solutions (SL)

Foliage wetting increasing activity (promotion of biological activity)

| MCPA K - salt (97%) | 412 g/l | — |
|---|---|---|
| Dichloroprop K-salt (95%) | — | 526 g/l |
| Component B | 20 g/l | — |
| Component S | — | 25 g/l |
| Water | ad 1 liter | |

4. Water soluble powder concentrate (SP)

Wetting agent, drop-spreading increasing effect.

| Cartapchloride (95%) | 42.1 mass % |
|---|---|
| Component M | 3 mass % |
| Powdered sugar | ad 100 mass %. |

Component M advantageously moderates the agglomerating tendency of the preparation formed with water soluble sugar due to its hygroscopic property, that is it ensures better storage.

5. Sprayable powders (WP)

| Wetting agent | | | | |
|---|---|---|---|---|
| Benomyl (95%) | 52.6 mass % | — | — | — |
| Carbendazim (97%) | — | 51.6 | — | — |
| Folpet (93%) | — | — | 50 | — |
| Copperoxychloride (50% copper) | — | — | 30 | — |
| Permetrin (95%) | — | — | — | 26 |
| Ultrasil VN 3 | 5 | 5 | 5 | 20 |
| Calciumcarbonate | ad 100 | — | — | — |
| Kaolin | — | ad 100% | ad 100% | ad 100% |
| Component E | 3.5 | 2 | — | — |
| Component Y | — | 2 | 3 | 3 |
| Borrespense 3 A | 3.5 | 3 | 5 | 4 | where Borrespense 3 A = sodium-lignin-sulphonate

6. Suspension concentrates (SC)

| | mass % | | | | | | |
|---|---|---|---|---|---|---|---|
| Flutriafol (98%) | 25.5 | — | — | — | — | — | — |
| Carbendazim (96%) | — | 20.9 | — | — | — | — | — |
| Carbofuran (93%) | — | — | 43 | — | — | — | — |
| Atrazine (97%) | — | — | — | 51.5 | — | — | — |
| Isoproturon (96%) | — | — | — | — | 47.5 | — | — |
| Chloridazon (92%) | — | — | — | — | — | 38.9 | — |
| Copperoxychloride (50% copper) | — | — | — | — | — | — | 6 |
| White oil | — | 20 | 8 | — | — | — | — |
| Component W | 0.5 | 1.5 | — | 0.4 | 0.4 | — | — |
| Component O | 0.5 | — | — | — | — | 0.8 | — |
| Component S | — | — | 1 | — | 0.2 | — | 1 |
| Propyleneglycol | 5 | 6 | 6 | 6 | 6 | 6 | 6 |
| Emulson AG/1314 | 0.5 | 0.3 | 0.5 | — | 0.5 | 2 | 0.5 |
| Emulson AG/6130 | 1.0 | 0.75 | 0.9 | 1 | 0.8 | — | 1.5 |
| Emulson AG/2527 | — | 1.2 | 0.9 | — | — | 0.5 | — |
| Madeol AG/2376 | 0.5 | 0.5 | 0.2 | 0.2 | 0.2 | 0.15 | 0.2 |
| Product 0028 | 0.5 | 0.4 | 0.5 | 0.5 | 0.5 | — | 0.5 |
| Water | ad 100% | ad 100% | ad 100% | ad 100% | ad 100% | ad 100% | ad 100% | where
Madeol AG/2376 = xanthan gum + silicic acid
Product 0028 = silicon oil emulsion (30%) antifoaming agent
Emulson AG/1314 = ethoxylated bisphenol (EO: 13)
Emulson AG/2527 = ethoxylated castor oil (EO: 25)
Emulson AG/6130 = triethanolamine salt of ethoxylated and phosphatized bisphenol (mixture of mono- and diphosphate, ethoxylation: 13 EO)

7. Wettable powders (WS)

| | mass % | | |
|---|---|---|---|
| Carbendazim (96%) | 52.1 | — | — |
| Folpet (93%) | — | 53.8 | — |
| Copper oxyquinolate (95%) | — | — | 52.6 |
| Ultrasil VN 3 | 5 | 5 | 5 |
| Mowinol 4/88 | 8 | 8 | 8 |
| Madeol AG/OR 95 | 2.5 | 3 | 3.5 |
| Component T | 3 | 2.5 | 3.5 |
| Irgalite-blue | 1 | 1 | 0.8 |
| Kaolin | | ad 100 | | where
Mowinol 4/88 = polyvinyl-alcohol (Hoechst)
Irgalite-blue = colouring agent

8. Suspension dressing agents (FS)

| | mass % | | |
|---|---|---|---|
| Carbendazim (96%) | 26.1 | — | — |
| Flutriafol (98%) | — | 12.8 | — |
| Copper oxyquinolate (95%) | — | — | 21.1 |

-continued

|  | mass % | | |
|---|---|---|---|
| Ethyleneglycole | 7 | 7 | 7 |
| Vinavil EVA 06 T | 18 | 18 | 18 |
| Component K | 1 | — | 0.3 |
| Component S | — | 0.8 | 0.3 |
| Emulson AG/1314 | 0.2 | 0.5 | — |
| Emulson AG/PE | 0.3 | 1.2 | — |
| Emulson AG/6130 | 0.5 | — | 1.5 |
| Madeol AG/2376 | 0.1 | 0.2 | — |
| Basasol ROT 76 L | 0.5 | 0.5 | 0.8 |
| Silison SRE | 0.7 | 0.7 | 0.5 |
| Water | ad 100 | | | where
Vinavil EVA 06 T = a film forming polymer polyvinylacetate derivative (Montedison)
Basasol ROT 76 L = a coloring component (BASF)
Silison SRE = an antifoaming agent in a silicone oil emulsion of 30% (Wacker).

9. Microemulsions (EW)
(a good stability between −5° C. and 54° C.)

|  | mass % | | |
|---|---|---|---|
| a.) Cypermetrin (90%) | 4.5 | 4.5 | — |
| Permetrin (95%) | — | — | 10.5 |
| PBO (90%) | — | 15 | — |
| Component B | 3.0 | — | 5.0 |
| Component O | 2.0 | 1.0 | — |
| Component S | — | 4.0 | — |
| Emulson AG/1314 | 12 | 15 | 14 |
| Emulson AG/0600 | 3 | 3 | 6 |
| Water | ad 100 | | | where
Emulson AG/0600 = Emulson AG/CAL (calcium-dodecyl-benzosulphonate)
PBO = piperonyl-butoxyde

|  | mass % | | | |
|---|---|---|---|---|
| b.) Cypermetrin-isomer (g/l) | | | | |
| - 1RcisS + 1ScisR | 20 | 20 | — | — |
| - 1RtransS + 1StransR | 30 | 30 | 50 | 50 |
| PBO | — | 100 | — | 100 |
| Ethyleneglycol | 90 | — | 90 | — |
| Propyleneglycol | — | 90 | — | 90 |
| Butanol | 50 | — | 40 | 30 |
| Ethanol | — | 40 | — | — |
| Component B | 60 | 50 | 40 | 60 |
| Component O | — | 10 | 10 | 90 |
| Component S | — | 5 | 10 | — |
| Emulson AG/1314 | 100 | 70 | 50 | 70 |
| Emulson AG/0600 | 60 | 40 | 50 | 60 |
| Water | ad 1000 ml | | | |

|  | mass % | | | | |
|---|---|---|---|---|---|
| c.) Quinalphos | 250 | 250 | 200 | — | 200 |
| Cypermetrin isomer | | | | | |
| -1RcisS + 1ScisR | — | — | 20 | — | — |
| - 1RtransS + 1StransR | — | — | 30 | 50 | 50 |
| Tetrametrin | — | — | — | 5 | — |
| PBO | — | — | — | 100 | — |
| Butly-hydroxytoluene | — | — | 10 | 10 | 10 |
| Solvesso | 200 | — | 10 | — | — |
| Butanol | 70 | 200 | 50 | 10 | 30 |
| Component B | 50 | — | 10 | — | 25 |
| Component O | 70 | — | — | 100 | — |
| Component S | — | 100 | 30 | — | 40 |
| Component H | — | 50 | — | 20 | — |
| Component I | — | 10 | — | — | 30 |
| Component M | — | — | 50 | — | 15 |
| Emulson AG/1314 | 40 | — | 10 | 50 | — |
| Water | ad 1000 ml | | | | |

10. Granulates dispersable in water (WG)
(promoting quick wetting)

| | | |
|---|---|---|
| Carbendazim (96%) | 78.1 mass % | — |
| Atrazine (97%) | — | 77.3 mass % |
| Component W | 3 mass % | — |
| Component B | 13 | 4.5 mass % |
| Emulson AG/0240 | 0.7 mass % | 0.5 mass % |
| Madeol AG/OR95 | 5 mass % | 5 mass % |
| Ultrasil VN 3 | 5 mass % | 5 mass % |
| Kaolin | ad 100% | |

Where Emulson AG/0240 = ethoxylated-bisphenol (EO: 24)

In the course of the preparation of the powderous mixtures consisting of the component above—after fine grinding—in the form of an aqueous solution the suitable quantity of the surface active ingredient according to the invention is sprayed in a granulating mixer (plate granulator).

11. Ultra ULV preparations
(Drop spreading and adhesion improving, active ingredient stabilizing, viscosity adjusting effect)

| | | |
|---|---|---|
| Cypermethrin (90%) | 11.1 mass % | — |
| Phosalome (95%) | — | 26.3 mass % |
| Solvesso 200 | 25.0 mass % | 35.0 mass % |
| Component I | 2.0 mass % | 2.0 mass % |
| Sunflower oil | ad 100 mass % | ad 100 mass % |

12. Microcapsule
(Control of the active ingredient release, influencing the capsule-preparation)

| | mass % |
|---|---|
| a.) Transmetrin | 12.62 |
| Tetrametrin | 1.24 |
| PBO | 86.14 |
| Poly-phenylisocyanate (31%) | 3.0 |
| Component I | 1.0 |
| Water | 32.9 |
| aqueous diluted-1,6-hexametylene-diamine solution (1,6-HMD aqueous 12.4% solution) | 3.0 |
| Ethyleneglycol | 15.7 |
| Component M | 1.0 |
| CaCl$_2$ | 3.0 |
| b.) Permetrin | 28.6 |
| Aromatol | 21.5 |
| Poly-phenylisocyanate | 3.5 |
| Component I | 1.1 |
| Water | 40.8 |
| HMD-diluted | 3.5 |
| CaCl$_2$ | 1.1 |
| c.) Permetrin | 29.0 |
| Solvesso 100 | 14.6 |
| Component I | 1.0 |
| Water | 35.6 |
| HMD-diluted | 3.0 |
| CaCl$_2$ | 5.0 |
| NaCl | 1.0 |
| Component M | 1.0 |
| d.) Cypermetrin:Aromatol 1:1 | 47.3 |
| Poly-phenylisocyanate | 3.3 |
| Component I | 1.0 |
| HMD-diluted | 3.3 |
| Ethyleneglycol | 4.9 |
| Water | 38.8 |
| CaCl$_2$ | 0.6 |
| Component P | 0.8 |
| e.) Cypermetrin:Aromatol 20:15 | 38.6 |
| Poly-phenylisocyanate | 2.7 |
| Component I | 0.9 |
| Water | 31.6 |
| HMD-diluted | 2.7 |

| | mass % |
|---|---|
| Ethyleneglycol | 23.0 |
| CaCl₂ | 0.5 |
| f.) Cypermetrin:Aromatol 20:15 | 48.0 |
| Poly-phenylisocyanate | 3.4 |
| Component I | 1.1 |
| Water | 39.5 |
| HMD-diluted | 3.4 |
| Ethyleneglycol | 2.4 |
| CaCl₂ | 0.6 |
| Component N | 1.2 |
| g.) Transmetrin-Solvesso 100 10:35 | 37.8 |
| Poly-phenylisocyanate | 2.9 |
| Component I | 1.6 |
| Water | 30.8 |
| HMD-diluted | 2.8 |
| Ethyleneglycol | 8.1 |
| CaCl₂ | 12.2 |
| NaCl | 3.3 |
| Component M | 0.8 |
| h.) Transmetrin:Solvesso 100:Xylene 10:16:5 | 49.3 |
| Poly-phenylisocyanate | 3.4 |
| Component I | 1.1 |
| Water | 40.0 |
| HMD-diluted | 3.4 |
| CaCl₂ | 2.8 |
| i.) Ekalux 50 | 38.3 |
| Poly-phenylisocyanate | 3.4 |
| Water | 40.0 |
| HMD-diluted | 3.4 |
| CaCl₂ | 2.8 |
| j.) EPTC | 36.3 |
| Poly-penylisocyanate | 2.5 |
| Component I | 1.6 |
| Water | 29.5 |
| HMD-diluted | 3.1 |
| NaCl | 1.6 |
| CaCl₂ | 3.1 |
| Component M | 0.8 |
| k.) Permetrin-Aromatol (20:15) | 47.5 |
| Poly-phenylisocyanate | 3.2 |
| Component I | 1.0 |
| Water | 38.1 |
| HMD-diluted | 3.2 |
| CaCl₂ | 5.0 |
| NaCl | 1.0 |
| Component N | 1.0 |

The microcapsules above were prepared by the following steps:

a.) the active ingredient and the poly-phenylisocyanate were kneaded to a homogenous phase;

b.) the surface active agent and the water were mixed to one phase;

c.) into the aqueous phase (b) the oily phase (a) was poured slowly, thereafter by turaxing slowly while cooling with water an emulsion was formed;

d.) to the emulsion the diluted HMD solution was added drop-by-drop, whereafter while cooling with water the mixture was turaxed;

e.) if necessary to the finished formulation ethyleneglycol was added and the suitable quantities of CaCl₂ and NaCl respectively, were added to adjust the viscosity.

13. Preparation for bathing animals

| Chinmix | 250 g/l |
|---|---|
| Component A | 70 g/l |
| Xylene | ad 1000 ml |

By mixing the mixture above in a ratio of 1:2-1:20 with phenolfree kreoline and diluting the same with a 500-2000 fold quantity of water a good stabilized emulsion for bathing animals is obtained.

Kreolin = mixture of coal oil, Na-iktiol, sodium hydroxide and canifol

14. Additive preparation containing no active ingredient

| a. Component X | |
|---|---|
| Potassium-mono-laurate-ethoxy(9)-tartarate | 40 mass % |
| Water | 60 mass % |
| b. Component B | |
| Sodium-mono-laurate-ethoxy(8)-citrate | 25 mass % |
| Water | 75 mass % |

15. Preparation of tankmixtures

Tankmixtures of the following compositions were prepared in a way, that the combination of a plant protecting agent and/or an artificial chemical fertilizer (from time to time in a prediluted form) is added to the additive preparation.

| | mass % | | |
|---|---|---|---|
| Component X | 2.0 | — | 1.5 |
| Component B | — | 3.0 | 1.5 |
| Fundazol 50 WP | 1.0 | — | — |
| Olitref EC | — | 1.2 | — |
| Dithiane M-45 | 1.0 | — | 0.7 |
| Carbamide | — | 15.0 | — |
| Sequestren 138 Fe | — | — | 1.0 |
| Water | | ad 100% | |

What we claim is:

1. A plant protecting composition, containing an active ingredient which is 0.1 to 10% by weight of a fungicide, herbicide, insecticide, nematocide, acaricide, and optionally a solid or liquid carrier, and at least one surface active agent of the formulae (I)

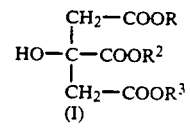

or (II),

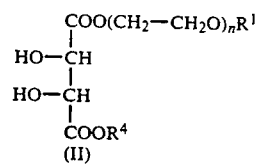

or a mixture thereof, wherein R, $R^2$, $R^3$ and $R^4$ are independently from each other hydrogen, an organic or inorganic cation or a group of the formula $-(CH_2-CH_2-O)_nR^1$, wherein $R^1$ is a $C_{10-20}$ alkyl group and n is an integer from 4 to 20, provided that at least one of R, $R^2$ and $R^3$ is a group of the formula $(CH_2-CH_2O)_nR^1$, in an amount effective to stabilize said plant-protecting active ingredient.

2. A plant protecting composition according to claim 1, formulated in the form of emulsion forming preparation (EC), sprayable powder (WP), dispersable granulate (WG), suspension concentrate (SC), ULV preparation, concentrated aqueous solution (SL), microemulsion (ES) or, capsule suspension (CS).

3. A veterinary, preparation, containing 0.1 to 10% by weight of a veterinary effective active ingredient which is a fungicide, insecticide, nematocide, or acaricide and a solid or liquid carrier, suitable for use in veterinary therapy, and 0.1-10 mass % of at least one surface active agent of the formulae (I)

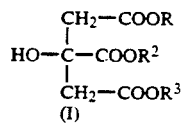

or (II),

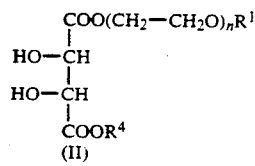

or a mixture thereof in which R, $R^2$, $R^3$ and $R^4$ are independently from each other hydrogen, an organic or inorganic cation, or a group of the formula $(CH_2-CH_2O)_nR^1$, $R^1$ is a $C_{10-20}$ alkyl group, n is an integer from 4 to 20, provided that at least one of R, $R^2$ and $R^3$ is a group of the formula $(CH_2-CH_2O)_nR^1$.

4. The veterinary preparation defined in claim 3 comprising 250 g of Chinmix as the veterinary effective active ingredient; 70 g of the surface active agent of the Formula (I) which is a monoester of citric acid wherein the esterifying moiety has the following formula:

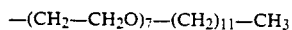

per liter of xylene as the liquid carrier.

5. A method of slowing down decomposition of a plant-protecting composition containing as a plant-protecting active ingredient, 0.1 to 10% by weight of a fungicide, herbicide, insecticide, nematocide, acaricide, or plant growth regulating agent, while at the same time exerting a wetting, solubilizing, or penetration-enhancing effect, which comprises the step of stabilizing said fungicide, herbicide, insecticide, nematocide, acaricide, or plant growth regulating agent, with a compound of the Formula (I)

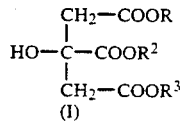

or (II),

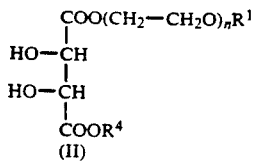

$R^1$, $R^2$, $R^3$ and $R^4$ are independently from each other, hydrogen, an organic or inorganic cation, or a group of the formula $-(CH_2-CH_2O)_nR^1$, wherein
$R^1$ is a $C_{10}$ to $C_{20}$ alkyl group, and
n is an integer from 4 to 20, provided that at least one of R, $R^2$, and $R^3$ is a group of the formula $-(CH_2-CH_2O)_nR^1$, in an amount effective to stabilize said plant-protecting active ingredient.

6. A method of slowing down decomposition of a veterinary composition containing as a veterinary active ingredient, 0.1 to 10% by weight of a fungicide, insecticide, nematocide, or acaricide, while at the same time exerting a wetting, solubilizing, or penetration-enhancing effect, which comprises the step of stabilizing said fungicide, insecticide, nematocide, or acaricide, with a compound of the Formula (I)

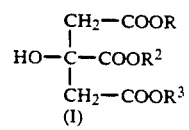

or (II),

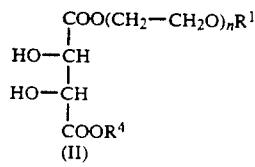

$R^1$, $R^2$, $R^3$ and $R^4$ are independently from each other, hydrogen, an organic or inorganic cation, or a group of the formula $-(CH_2-CH_2O)_nR^1$, wherein
$R^1$ is a $C_{10}$ to $C_{20}$ alkyl group, and
n is an integer from 4 to 20, provided that at least one of R, $R^2$, and $R^3$ is a group of the formula $-(CH_2-CH_2O)_nR^1$, in an amount effective to stabilize said veterinary active ingredient.

7. The method of slowing down decomposition of a veterinary composition defined in claim 5 wherein the active ingredient is an insecticide selected from the group consisting of permethrin, cypermethrin, deltamethrin, bifenthrin, fenpropathrin, chinmix and transmethrin.

* * * * *